United States Patent [19]

Chiesi

[11] Patent Number: 5,017,607
[45] Date of Patent: May 21, 1991

[54] METHOD TO TREAT PARKINSONS DISEASE

[75] Inventor: Paolo Chiesi, Parma, Italy

[73] Assignee: Chiesi Farmaceutici S.p.A., Parma, Italy

[21] Appl. No.: 374,273

[22] Filed: Jun. 30, 1989

Related U.S. Application Data

[63] Continuation of Ser. No. 56,372, Jun. 1, 1987, abandoned.

[30] Foreign Application Priority Data

Jun. 10, 1986 [IT] Italy ............................. 20737 A/86
Jan. 30, 1987 [IT] Italy ............................. 19221 A/87

[51] Int. Cl.$^5$ .............................................. A61K 31/24
[52] U.S. Cl. .................................... 514/534; 514/535
[58] Field of Search ............................... 514/534, 535

*Primary Examiner*—Stanley J. Friedman
*Attorney, Agent, or Firm*—Bucknam and Archer

[57] ABSTRACT

Pharmaceutical compositions for the treatment of Parkinson's disease and neurologic syndromes connected with it, containing as the active principle levodopa methyl ester optionally combined with other active principles selected from dopaminergic, anticholinergic, antidepressive drugs, carboxylase and monoaminoxidase inhibitors.

1 Claim, No Drawings

METHOD TO TREAT PARKINSONS DISEASE

This is a continuation of application Ser. No. 056,372, filed June 10, 1987, now abandoned.

The present invention refers to pharmaceutical compositions for the treatment of Parkinson's disease, containing levodopa methyl ester alone or combined with other active principles.

Parkinson's disease is characterized by a progressive degeneration of the dopaminergic nigrostriatal pathways in the brain.

Biochemical studies carried out in the sixties lead to the discovery of the fundamental role played in the pathogenesis of this disease by the deficit of neurotransmitters, and particularly of dopamine.

This important advance in the comprehension of the neurochemical bases of the pathology brought about a drastic change in the pharmacological approach to the disease, and lead to the introduction in the therapy of an immediate biologic precursor of dopamine, (−)-3-(3,4-dihydroxyphenyl)-L-alanine, more commonly known as levodopa.

The use of levodopa lead to a dramatic improvement in the treatment of parkinsonism, and it is still the treatment of choice of this disease.

Chronic treatment per os, however, often leads to a progressive decrease of the therapeutic effectiveness and to the onset of serious unwanted effects, including abnormal involuntary movements, "end-of-dose deterioration" when efficacy is limited to 3–4 hours, and the "on-off" phenomenon—marked, very abrupt, almost instantaneous, changes in the level of disability.

Pharmacokinetic factors, such as variability in the plasma concentration and interference with intestinal absorption of levodopa due to competition with proteins and amino acids, appear to play a primary role in the origin of the late complications from levodopa therapy, particularly the "on-off" fluctuations.

Alternative therapies with dopaminergic drugs, such as bromocriptine, do not give actual advantages in prevention or reduction of response fluctuations.

The importance of the pharmacokinetics of levodopa for the fluctuating clinical response has been emphasized by studies in which levodopa plasma levels are stabilized by administering the drug via constant intravenous infusion. Under these conditions, a stable clinical response can be maintained for hours.

Levodopa itself, however, is not suitable for long-term systemic use, since it is slightly soluble and can therefore only be administered in large volumes of solvents.

In spite of having been known for a long time, levodopa methyl ester has never been used in human therapy, even though, since 1965, Hanson L. C. F. and Utley J. D. showed, in reserpine-treated cats, by measuring brain catecholamine levels and assessing the behavior evaluation in the conditioned avoidance response, that levodopa methyl ester causes the same effects as levodopa (Psychopharmacologia 8; 140–144, 1965).

Recently other experimental patterns have confirmed that levodopa methyl ester is as active as the starting compound, so that it has been suggested as a suitable candidate for the chronic infusion in parkinsonian patients (Cooper D. R. et al, Clin. Neuropharmacol. 7 (1), 89–98, 1984).

It has now been found that levodopa methyl ester, hereinafter referred to LDME, can be used as active principle of particular pharmaceutical compositions with surprising therapeutic effects.

A main object of the present invention refers therefore to pharmaceutical compositions containing LDME for the treatment of all kind of parkinsonism and in the neurologic syndromes related to it.

Such compositions can be administered by oral, buccal, sublingual, parenteral, rectal routes, or by means of portable system capable of infusing small volumes of the drug by subcutaneous route.

Pharmaceutical compositions for oral administration can be solid or liquid.

LDME, in fact, thanks to its high solubility, can be successfully used for the preparation of aqueous pharmaceutical compositions, at the desired concentrations and in small administration volumes.

Solid pharmaceutical compositions for oral administration, in the form of capsules or tablets of similar formulations, can be prepared according to traditional methods.

The unit dose may range from 100 to 1.000 mg of active principle.

Liquid pharmaceutical compositions for oral administration can be prepared by dissolving LDME in a suitable aqueous medium.

The solution may also contain a preserving agent with antioxidant chelant or antibacterial action, examples of such additives being ascorbic acid, sodium metabisulfite, citrates, p-hydroxybenzoates, etc.

Other additives, such as buffers, viscosity regulators, sugars, cosolvents, flavoring agents, can be added to the formulations.

Alternatively, the compositions can be prepared from powdered or granulated mixtures to be reconstituted with water at the moment of use.

These compositions in form of mono-dose or multidose may contain the active ingredient in concentration up to 400 mg/ml.

Solid or liquid compositions as described above can be administered by oral or sublingual way.

The sublingual route of LDME administration proved to be rational and effective and grants remarkable advantages:
more rapid and reliable absorption than from the gastrointestinal tract;
bypass of the hepatic circulation;
possibility of being employed in gastroresected subjects or, in general, in patients with impaired absorption.

Another very suitable system of LDME administration is the buccal delivery by small tablets which adhere to the surface of the oral mucosa releasing drug amounts constant in time, assuring steady plasmatic levels and consequently avoiding fluctuating clinical responses.

Parenteral compositions can be formulated in the conventional manner with suitable pharmaceutical adjuvants and may contain the active ingredient in concentration up to 250 mg/ml.

Moreover, particularly surprising is the possibility to administer LDME by rectal route.

On the contrary to its precursor levodopa, which is not absorbed by rectal mucosa, LDME does produce, by rectal administration detectable plasma levels sufficient to assure a therapeutic effect.

Pharmaceutical compositions for rectal administration may contain a range of the active ingredient from 100 to 1.000 mg per unit dose.

In order to improve the therapeutic action, LDME may also be advantageously used in combination with other active principles, selected from peripheral decarboxylase inhibitors, such as carbidopa or benserazide, or selective MAO-B inhibitors, such as deprenyl.

The combined regimens:
(a) LDME+decarboxylase inhibitors;
(b) LDME+MAO-B inhibitor;
(c) LDME+decarboxylase inhibitor+MAO inhibitor, allow a remarkable reduction in the dose of LDME necessary to control the disease, consequently decreasing side effects, with a prolongation and an increase of effectiveness and with a more rapid pharmacological response.

To allow the application of the therapeutic and posological scheme more suited to a particular pathological condition, LDME and the above mentioned active principles may be administered separately.

Alternatively, the patient may be administered with therapeutic compositions containing as active principles both LDME and a peripheral decarboxylase inhibitor and/or a MAO-B inhibitor or optionally with both of them.

Solid compositions for oral, buccal, sublingual or rectal administration may contain as the active principle LDME in an unit dose ranging from 100 to 300 mg in combination with benserazide, in a ratio between 2:1 and 5:1, or in combination with carbidopa, in a ratio ranging from 4:1 to 10:1, and they may be extemporaneously administered in combination with oral pharmaceutical compositions, containing as the active principle deprenyl, in a quantity of 5 mg per unit dose.

Liquid compositions may contain LDME in a concentration ranging from 50 to 400 mg/ml in combination with benserazide, in a ratio ranging from 2:1 to 10:1, or with carbidopa in a ratio ranging from 4:1 to 20:1, or with deprenyl, in a ratio ranging from 20:1 to 100:1, or, again, in association with benserazide and deprenyl, in ratios respectively ranging from 2:1:0.1 and 10:1:0.1 with carbidopa and deprenyl in ratios respectively ranging from 4:1:0.2 to 20:1:0.2.

Said pharmaceutical compositions may ensure an immediate release of active principles, or may be formulated to allow a planned and sequential release of components.

The following examples illustrate the invention in more details, without, however, limiting it.

Compositions containing LDME as the active ingredient

EXAMPLE 1

| Ready solution administrable by drops. | |
|---|---|
| Levodopa methyl ester | mg 250 |
| Methyl p-hydroxybenzoate | mg 1.35 |
| Propyl p-hydroxybenzoate | mg 0.15 |
| Saccharin sodium | mg 10 |
| Orange flavour | ml 0.002 |
| Citric acid H$_2$O | mg 20 |
| Trisodium citrate dihydrate | mg 31.5 |
| Purified water | q.s to ml 1 |

The solution in example 1 may be optionally added with an antioxidant such as sodium metabisulfite in quantity of mg 1.5; a sugar such as sucrose in quantity of mg 100; a co-solvent such as glycerol in quantity of mg 20.

EXAMPLE 2

| Powder composition to be reconstituted when used. | |
|---|---|
| Levodopa methyl ester HCl | mg 2.500 |
| Trisodium citrate dihydrate | mg 50 |
| Saccharin sodium | mg 100 |
| Saccharose | mg 1.000 |
| Flavouring powder | q.s. |
| To be reconstituted with water | ml 10 |

EXAMPLE 3

| Tablets for sublingual administration | |
|---|---|
| Levodopa methyl ester | mg 200 |
| Gum arabic | mg 10 |
| Lactose | mg 90 |
| Ammonium glycyrrhizinate | mg 20 |
| Saccharin sodium | mg 10 |
| Flavour | mg 13 |
| Magnesium stearate | mg 7 |

Compositions containing LDME in combination with other active ingredients

EXAMPLE 4

| Ready solution to be administered by drops | |
|---|---|
| Levodopa methyl ester HCl | mg 250 |
| Levodeprenyl (HCl) | mg 2.5 |
| Methyl p-hydroxybenzoate | mg 1.35 |
| Propyl p-hydroxybenzoate | mg 0.15 |
| Saccharin sodium | mg 10 |
| Orange flavour | ml 0.002 |
| Citric acid H$_2$O | mg 20 |
| Trisodium citrate dihydrate | mg 31.5 |
| Purified water | q.s. to ml 1 |

As per Example 4 above, by using similar adjuvants in the specified quantities, compositions containing as active ingredients LDME in combination with peripheral decarboxylase inhibitors and/or MAO inhibitors in the quantities listed herebelow, may be prepared.

EXAMPLE 5

| Ready solution to be administered by drops | |
|---|---|
| Levodopa methyl ester HCl | mg 100 |
| Benserazide HCl | mg 19 |

EXAMPLE 6

| Ready solution to be administered by drops | |
|---|---|
| Levodopa methyl ester HCl | mg 100 |
| Carbidopa HCl | mg 9.5 |

EXAMPLE 7

| Ready solution to be administered by drops | |
|---|---|
| Levodopa methyl ester | mg 100 |
| Levodeprenyl HCl | mg 1 |

-continued

| Ready solution to be administered by drops | |
|---|---|
| Benserazide HCl | mg 11.4 |

EXAMPLE 8

| Ready solution to be administered by drops | |
|---|---|
| Levodopa methyl ester HCl | mg 100 |
| Levodeprenyl HCl | mg 1 |
| Carbidopa HCl | mg 5.74 |

The pharmaceutical composition as per Example 1 above has been orally administered to parkinsonian patients manifesting the on-off phenomenon, in order to evaluate the bioavailability and the clinical effect of LDME in this formulation in comparison with levodopa.

As previously illustrated, patients manifesting the on-off phenomenon alternate between periods when parkinsonian signs are relatively severe and intervals when parkinsonism is largely, if not completely, replaced by involuntary movements.

The results have been very surprising.

The absorption of LDME was in fact very rapid, reaching the maximum concentration peak at 40–45 minutes from the administration.

Table 1 shows the single data of the levodopa plasmatic levels at the different times after administration respectively of LDME and levodopa in two patients.

TABLE 1

Levodopa plasmatic levels after single oral administration of corresponding doses of active principle (mg 200) respectively of LDME and levodopa in two patients.

| Time in minutes | Plasmatic levels ($\mu g/ml$) | | | |
|---|---|---|---|---|
| | Patient A | | Patient B | |
| | LDME | LD | LDME | LD |
| 0 | 0 | 0 | 0 | 0 |
| 15 | 0.87 | 0.31 | 0.36 | 0.35 |
| 30 | 1.45 | 1.05 | 0.95 | 0.66 |
| 45 | 1.50 | 1.41 | 1.67 | 0.88 |
| 60 | 1.05 | 1.13 | 1.29 | 1.15 |
| 80 | 0.89 | 1.47 | 1.12 | 1.67 |
| 100 | 0.88 | 1.17 | 0.86 | 1.39 |
| 120 | 0.72 | 0.93 | 0.82 | 1.35 |
| 140 | 0.63 | 1.03 | 0.66 | 1.05 |
| 160 | 0.51 | 0.82 | 0.62 | 0.82 |
| 180 | 0.46 | 0.65 | 0.43 | 0.80 |
| 210 | 0.43 | 0.70 | 0.44 | 0.58 |
| 240 | 0.35 | 0.49 | 0.21 | 0.45 |
| 270 | 0.25 | 0.35 | 0.20 | 0.38 |
| 300 | 0.21 | 0.28 | 0.14 | 0.17 |
| 330 | 0.20 | 0.42 | | |

The rapid attainment of high concentrations of Levodopa in the systemic circulations after LDME administration produces a very early onset of the therapeutic effect, which appears at 20–30 minutes about from the administration of the composition as per Example 1 of the invention.

Moreover, the duration of action noticed as "on" period duration, was superior with LDME in respect to the levodopa.

A further advantage linked with the therapeutic action of LDME which came out from these preliminary trials, consists in that the drug in this composition and by this route of administration does not seem to induce dyskinesias at the moment of the appearance of the mobility ("on" phase) in the subjects presenting the "long-term syndrome", the phenomenon which occurs in about half of parkinsonian patients treated for 3–5 or more years.

Much more surprising have been the results obtained by administering the composition as per Example 1 by sublingual route.

By this way, in fact, the absorption of the active principle is much more rapid and, the onset of the therapeutic effect is much more early and persistent (table 2).

TABLE 2

Therapeutic effects in idiopathic parkinsonian patients presenting "on-off" phenomenon determined as time of turn "on" and as duration of the "on" period.
Comparison between two treatment regimens:
I. LDME mg 200 sublingual administration + mg 25 of carbidopa oral administration.
II. Sinemet ® mg 275 oral administration (mg 250 of levodopa + mg 25 of carbidopa).

| | TREATMENT | | | |
|---|---|---|---|---|
| | I | | II | |
| | sublingual LDME 200 mg + oral carbidopa mg 25 | | Sinemet ® mg 25 | |
| Patient N. | "on" onset (minutes) | "on" duration (minutes) | "on" onset (minutes) | "on" duration (minutes) |
| 1 | 40 | 150 | — | — |
| 2 | 35 | 175 | — | — |
| 3 | 45 | 140 | 65 | 165 |
| 4 | 35 | 195 | 60 | 165 |
| 5 | 40 | 190 | 40 | 200 |
| 6 | 45 | 205 | — | — |

LDME, particularly in certain administration forms and routes such as oral in liquid form sublingual or buccal, has demonstrated to be a valid therapeutic alternative for Parkinson's disease treatment, thanks to the particular advantages in comparison to levodopa.

The sublingual and buccal routes of administration, by passing the gastrointestinal system, may become the preferred approach for the treatment of patients with gastrointestinal problems.

Another very suitable administration technique of LDME is through a portable system capable of infusing small volumes of the drug by subcutaneous or intraperitoneal route.

I claim:

1. The method of treatment of Parkinson's disease and related neurological syndromes which consists of administering by the oral or sublingual route to a patient in need of said treatment an aqueous solution containing 250 mgs of LDME levodopa methyl ester as the active ingredient and onset of therapeutic effect is produced with a single dose after 20–30 minutes.

* * * * *